(12) United States Patent
Wysocki

(10) Patent No.: US 11,096,973 B2
(45) Date of Patent: Aug. 24, 2021

(54) HERBAL DECARBOXYLATION AND INFUSION SYSTEM

(71) Applicant: Dennis Wysocki, Middletown, DE (US)

(72) Inventor: Dennis Wysocki, Middletown, DE (US)

(73) Assignee: Dennis Wysocki, Middleton (DE)

( * ) Notice: Subject to any disclaimer, the term of this patent is extended or adjusted under 35 U.S.C. 154(b) by 0 days.

(21) Appl. No.: 16/734,910

(22) Filed: Jan. 6, 2020

(65) Prior Publication Data
US 2020/0215135 A1    Jul. 9, 2020

Related U.S. Application Data

(60) Provisional application No. 62/788,600, filed on Jan. 4, 2019.

(51) Int. Cl.
*A61K 36/00*    (2006.01)
*A23L 33/105*   (2016.01)
*B01D 11/02*    (2006.01)

(52) U.S. Cl.
CPC ............ *A61K 36/00* (2013.01); *A23L 33/105* (2016.08); *B01D 11/0207* (2013.01); *B01D 11/0288* (2013.01); *A23V 2002/00* (2013.01)

(58) Field of Classification Search
CPC ..................................................... A61K 36/00
USPC ......................................................... 424/725
See application file for complete search history.

(56) References Cited

U.S. PATENT DOCUMENTS

2020/0390838 A1 * 12/2020 Kotra .................. B01D 11/0211

* cited by examiner

*Primary Examiner* — Michael V Meller
(74) *Attorney, Agent, or Firm* — The Rapacke Law Group, P.A.; Andrew S. Rapacke

(57) ABSTRACT

A system for decarboxylating and infusing an organic material includes a decarboxylation and infusion apparatus is provided. The apparatus includes a heated reservoir in operable communication with a user interface whereon a user selects decarboxylation and infusion settings. The heated reservoir has a mixing element to agitate an organic material and solvent disposed therein as well as a filter to filter the organic material following the infusion.

1 Claim, 5 Drawing Sheets

HERBAL DECARBOXYLATION AND INFUSION SYSTEM

CROSS-REFERENCE TO RELATED APPLICATIONS

The present application claims priority to U.S. Provisional Application No. 62/788,600 filed on Jan. 4, 2019, entitled "HERBAL DECARBOXYLATION AND INFUSION SYSTEM" the entire disclosure of which is incorporated by reference herein.

TECHNICAL FIELD

The embodiments presented relate to systems for the automated decarboxylation of organic material and infusing the organic materials in a solvent.

BACKGROUND

The process of infusing solvents such as oils, fats, or alcohols with an organic material has been used to allow for or alter the delivery of organic material to a consumer. It is known that cannabis contains the medically useful molecules of cannabidiolic acid (CBDA), tetrahydrocannabinolic acid (THCA), and various other similar molecules. These molecules must be decarboxylated to yield Cannabidiol (CBD) and Tetrahydrocannabinol (THC), which are biologically active.

Following decarboxylation, the activated CBD and THC can be infused with a solvent for delivery to the consumer. Common solvents include butter, cooking oils, alcohols, glycerin, and other solvents having similar chemical properties. The infusion process binds the trichomes and plant-based oils into the solvent following a period of time and the introduction of heat and/or pressure.

The process of decarboxylation of cannabis has historically been performed using essential cookware and kitchen appliances. While some devices have been created to aid in decarboxylation or infusion, the currently available options are messy, odiferous, inflexible, inaccurate, and require multiple pieces of equipment for proper execution.

SUMMARY OF THE INVENTION

The embodiments disclose a system for decarboxylating and infusing an organic material comprising a decarboxylation and infusion apparatus. The apparatus includes a heated reservoir in operable communication with a user interface wherein a user selects from a plurality of pre-determined decarboxylation and infusion settings. The heated reservoir has a mixing element to agitate an organic material and solvent disposed of therein. The apparatus provides a means for decarboxylating and infusing organic materials into a biologically active material using a single apparatus and forgoing the need for additional tools and processes.

The apparatus facilitates the activation of molecules via decarboxylation to produce a biologically active infused solvent. The infused solvent can be used as a foodstuff, additive, topical, or other delivery mechanism depending on the molecular configuration, which is then infused into the solvent.

The decarboxylation and infusion apparatus described herein provides a means for a semi-automated system for performing the chemical processes of decarboxylating an organic material and infusing the decarboxylated organic material into a solvent for various applications, including consumption by a human. The apparatus may be provided as a single contained unit within a housing to prevent contamination, or undue transfer of the raw or processes materials.

In one aspect, the user interface is provided on a smart device in wireless communication with the decarboxylation and infusion apparatus.

In another aspect, the infusion setting is comprised of a time setting and a temperature setting allowing the user to control the type of infusion and potency of the final infused solvent product.

In one aspect, the solvent is comprised of at least one of the following: oil, butter, alcohol, or glycerin.

In another aspect, a user performs the steps of disposing an amount of the organic materials into the reservoir of the decarboxylation and infusion apparatus. The reservoir is then sealed, and a decarboxylation option is selected via the user interface. The decarboxylation is started, and once complete, the reservoir is opened, and the solvent is disposed of therein. The reservoir is sealed once more, and the organic material is infused with the solvent following the selection of a time and temperature option. Following the infusion protocol, the organic material is filtered to isolate the infused solvent.

In one aspect, the infused solvent is provided as a foodstuff, a beverage, a tonic, an elixir, a topical, a tincture, a liquid, a gel, or an aerosol.

BRIEF DESCRIPTION OF THE DRAWINGS

A complete understanding of the embodiments and the advantages and features thereof will be more readily understood by reference to the following detailed description when considered in conjunction with the accompanying drawings wherein.

DETAILED DESCRIPTION

Figure 1:
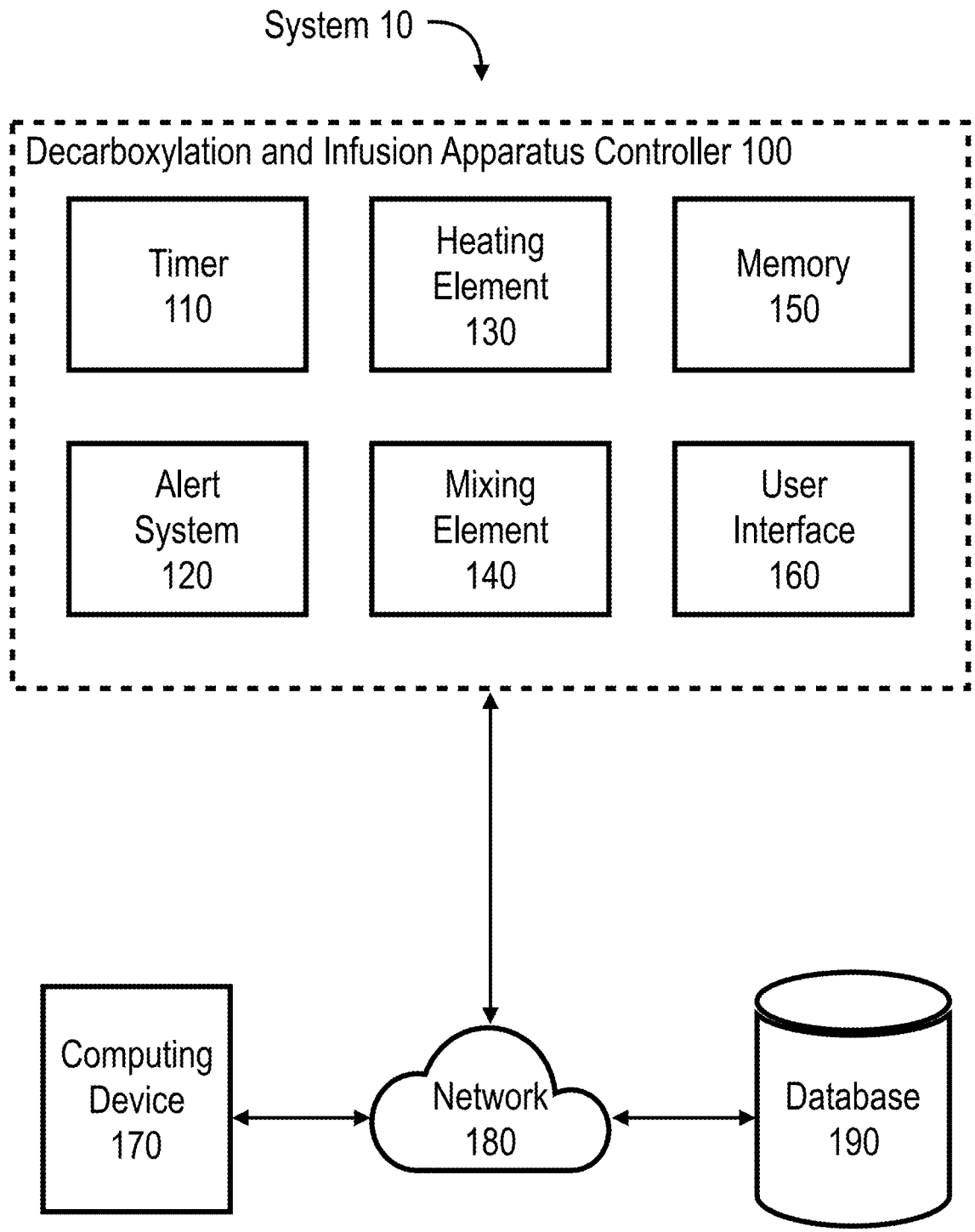
FIG. 1 illustrates a block diagram of the decarboxylation and infusion apparatus components, according to some embodiments.

The specific details of the single embodiment or variety of embodiments described herein are set forth in this application. Any specific details of the embodiments are used for demonstration purposes only, and no unnecessary limitation or inferences are to be understood therefrom. It is noted that the embodiments reside primarily in combinations of components related to the system and method of use thereof.

The present embodiments are based in part upon extraction procedures and delivery approaches that allow selective utilization of various cannabinoid molecules and terpenes from the cannabis plant. These various cannabinoid compounds are designed to selectively affect various cannabinoid receptors in the nervous system, immune system, and other tissues. The extract is an oil-based or solvent-based plant product that contains inactive and active compounds contained in the cannabis plant such as cannabinoids, terpenes, and/or flavonoids. Compositions of the invention and methods of extraction disclosed herein provide an extract with specific physiological properties that are mediated through separate pathways and receptors, which provide numerous benefits and advantages.

The extracts and/or delivery methods of the embodiments allow a wide range of prevention, treatment, and management options for patients. In some aspects, the delivery methods of the invention allow for employing micro-dosing with a stacking method of cannabinoid administration week-by-week until a certain saturation point, which is based on the response, weight, and monthly-quarterly test results. One skilled in the arts will readily understand the variety of product configurations and delivery mechanisms that may be produced using the embodiments.

It has been found that the age of the cannabis plant material in addition to the temperature in which it is stored and processed is critical. Importantly, for an extract to produce psychoactive properties or other significant properties found as a result of the consumption of decarboxylated molecules, the cannabis plant material is heated above 160° F.

Further the embodiments provided herein relate to a decarboxylation and infusion apparatus to produce an infused solvent. The apparatus decarboxylates organic material such as cannabis to activate molecules contained in the plant material. In one example, the apparatus is used to decarboxylate Cannabidiolic acid (CBDA) and Tetrahydrocannabinolic acid (THCA) into Cannabidiol (CBD) and Tetrahydrocannabinol (THC). One skilled in the arts will appreciate that various molecules contained in cannabis will readily undergo similar decarboxylation.

To facilitate decarboxylation, the apparatus is comprised of a heating element that can be selectively programmed to heat a reservoir containing the organic material to a specific temperature or temperature range. The heating element is further utilized to facilitate the infusion of the decarboxylated molecules into a solvent. It is known that infusion of molecules, including CDB and/or THC, is accomplished in a solvent such as cooking oils, glycerin, butter, or alcohol.

In some embodiments, the apparatus is in operable communication with a computing device that allows the user to control the function and operational settings of the apparatus during use. A mobile app may be downloaded to the computing device having a processor configured to perform instructions stored in a database. The database can include operational settings such as decarboxylation and infusions times, temperatures, pressures, agitation cycles, and protocols.

In some embodiments, the database may include a list of decarboxylation and infusion protocols for various recipes. Each recipe may be specific to one or more molecules, one or more organic materials, one or more solvents, and combinations thereof. Selecting a recipe may cause the apparatus to autonomously execute the instructions thereof.

In reference to FIG. 1, the system 10 for decarboxylating and infusing organic materials includes a decarboxylation and infusion apparatus controller 100 configured to produce a usable infused product which may be ingested or otherwise delivered to the user. The apparatus controller 100 may operate without the use of auxiliary tools or appliances. The apparatus controller 100 is in operable communication with a timer 110, alert system 120, heating element 130, and a mixing element 140, which are programmable to carry out procedures for decarboxylating and infusing organic materials. The heating element 130 provides heat to a reservoir wherein the organic material is decarboxylated and infused. The mixing element 140 is provided within the reservoir to agitate the organic material and promote uniform heating during decarboxylation and infusion protocols. A memory 150 stores operational settings for the apparatus controller 100 for various organic materials and infused solvent products that can be created. Each operational setting is selectable using a user interface 160 provided on the apparatus 100 or a computing device 170 in communication with the user. Network 180 transmits and receives data to and from the computing device 170 and database 190 to the apparatus controller 100.

In some embodiments, instructions for operational settings are stored in the database, which can include hardware components or cloud-based data storage. The computing device displays selectable options to the user, which are transmitted via the network to operate the apparatus.

In some embodiments, the alert system alerts the user using the apparatus and/or the computing device upon completion of the decarboxylation and infusion protocols. Alerts can include any audio or visual means known in the arts.

Figure 2:
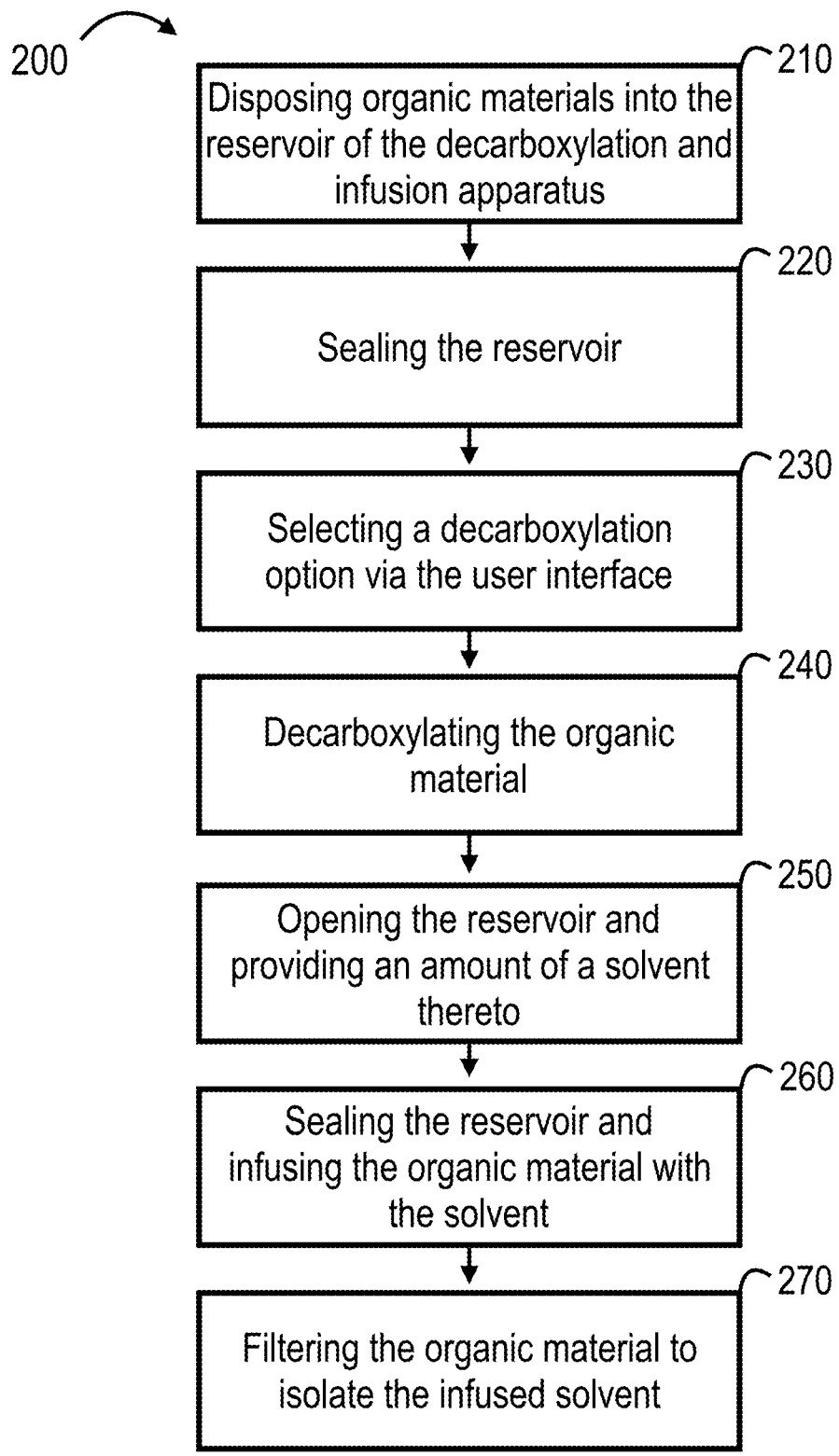
FIG. 2 illustrates a flowchart of a method for decarboxylating and infusing an organic material with a solvent using the decarboxylation and infusion apparatus, according to some embodiments.

FIG. 2 illustrates a method of use 200 of the apparatus. In step 210, the user disposed of organic materials into the reservoir of the decarboxylation and infusion apparatus 100. In step 220, the reservoir is sealed, and the user selects a suitable decarboxylation protocol using a user interface in step 230. The decarboxylation protocol may be altered depending on the organic material used and molecule to be decarboxylated. Following the decarboxylation protocol in step 240, the reservoir is opened, and a solvent is provided in step 250. In step 260, the reservoir is sealed, and the organic material is infused with the solvent to produce an infused solvent product. In step 270, the organic material is filtered to isolate the infused solvent, which can then be added to a foodstuff, beverage, topical, or another delivery mechanism.

In some embodiments, the user may select for isolation of one or more molecules by selecting an infusion pressure, an infusion temperature, one or more solvents, and infusion time. For example, the user can select to infuse CBD into the solvent without THC to reduce the psychoactive effects of the infused solvent.

Figure 3:
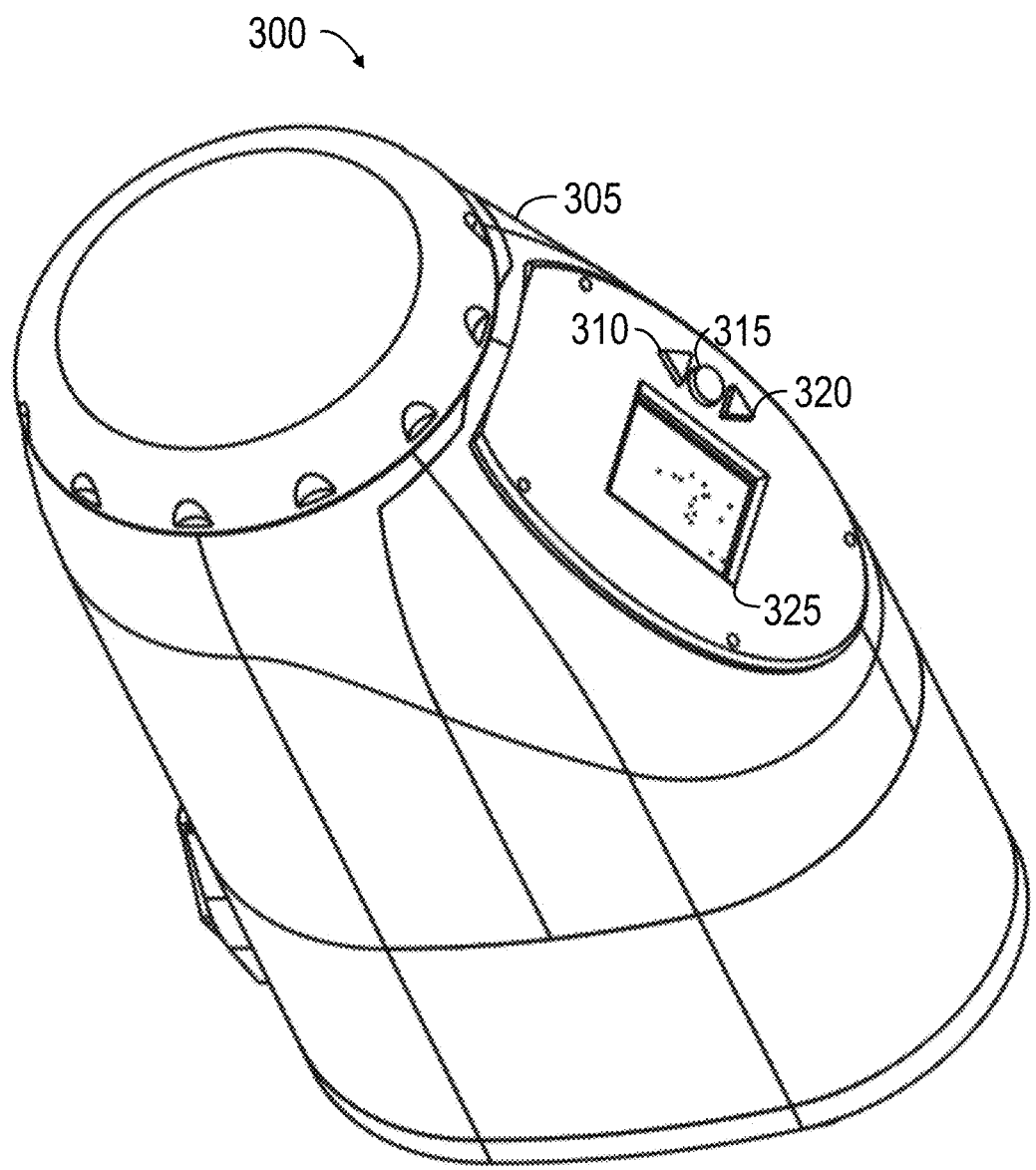
FIG. 3 illustrates a perspective view of the decarboxylation and infusion apparatus, according to some embodiments.
Figure 4:
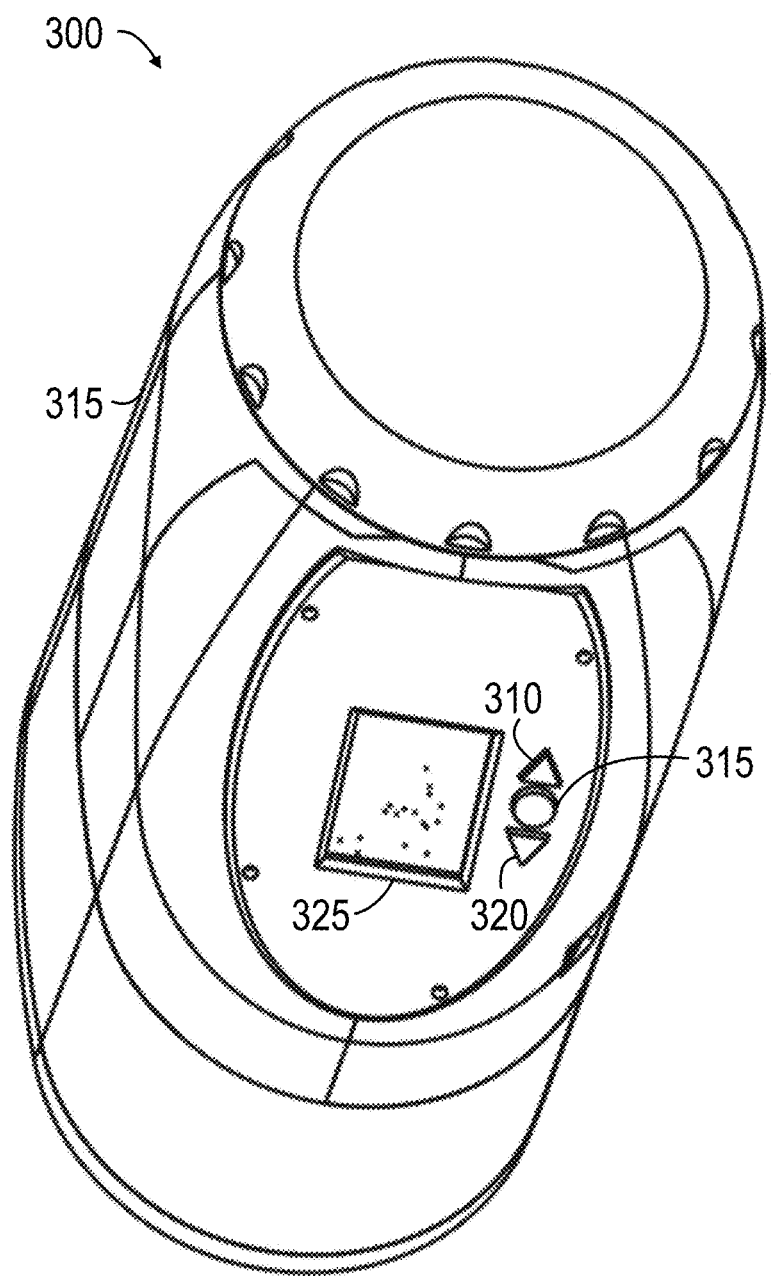
FIG. 4 illustrates a perspective view of the decarboxylation and infusion apparatus, according to some embodiments.

FIG. 3 and FIG. 4 illustrate the decarboxylation and infusion apparatus 300 comprising a housing 305 having controls 310, 315, 320 (collectively referred to as "controls"), and interface 325. Each of the controls permits the user to interact with the interface 325 to select various functionalities and operational parameters of the decarboxylation and infusion apparatus 300 to effectively decarboxylate and/or infuse or otherwise prepare the organic material.

Figure 5:
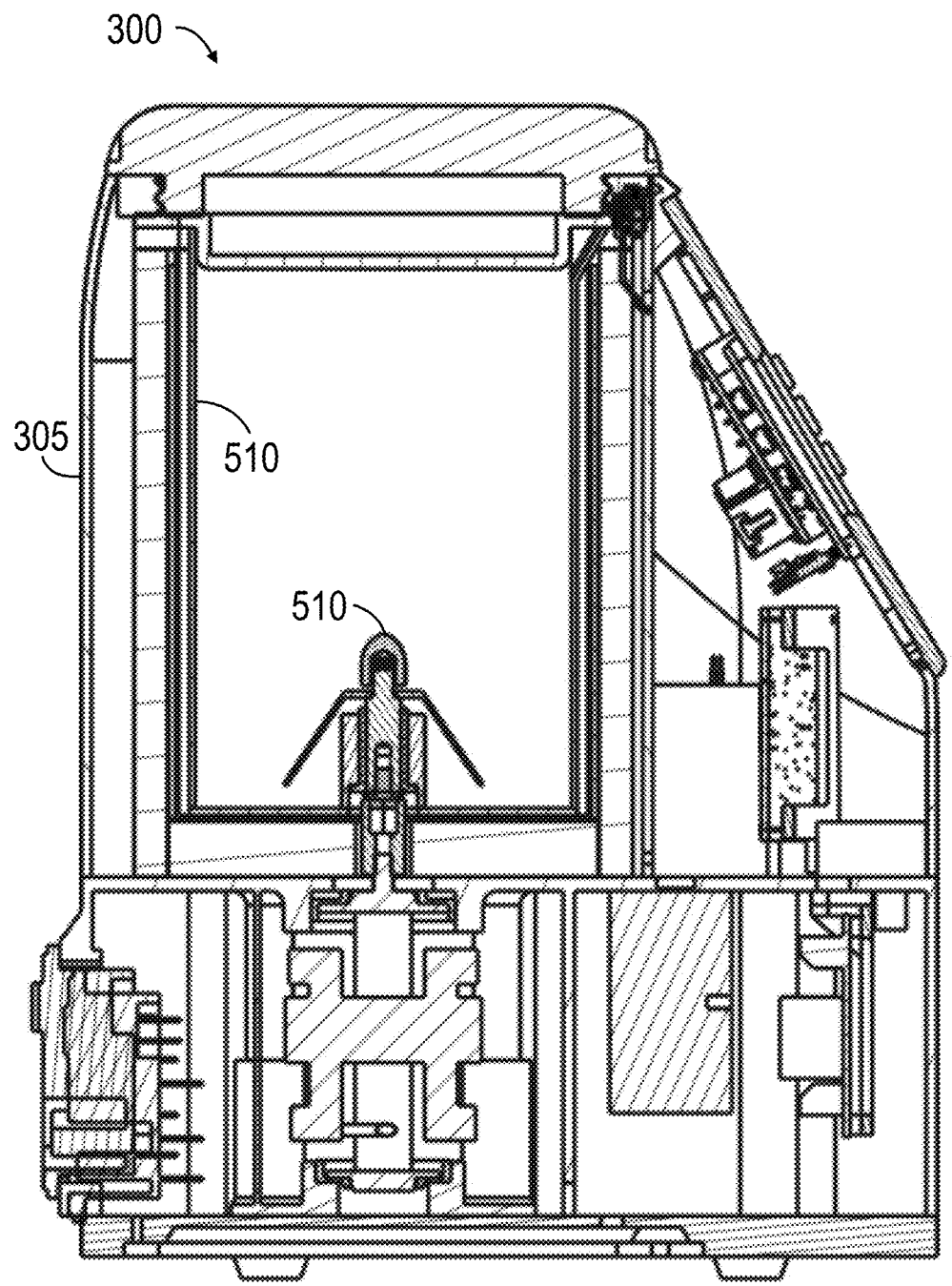
FIG. 5 illustrates a cross-section view of the internal components of the decarboxylation and infusion apparatus.

FIG. 5 illustrates a cross-section view of the decarboxylation and infusion apparatus 300 to show the housing 305 and the internal components thereof. A mixing element 505 is provided within a heated reservoir 510 to agitate organic material and a solvent disposed of therein. One skilled in the arts will readily understand that the organic material and solvent may change depending on the application of the product.

In some embodiments, the heated reservoir is at least partially surrounded or encapsulated by an insulative layer to thermally isolate the heated reservoir and the product therein within the apparatus from the environment and its ambient heating conditions as well as to evenly distribute the heat. An airtight lid may be provided to prevent oxygen from entering mixing chamber during the decarboxylation and infusion processes, minimize evaporation, and reduce odors.

The housing may be constructed of a variety of materials which are suitable, including, but not limited to, plastic, glass, silicone, food-grade butyl rubber, latex, aliphatic polyesters, natural rubber, metal, metal foils, polytetrafluoroethylene, biopolymers such as liquid wood, modified casein, polyhydroxyalkanoate polyesters, including polyhydroxybutrate, polyhydroxyvalerate, polylactic acid, starch-based polyesters, keratin processed with methyl acrylate, hemp polymers, hemp plastic, hemp composite polymers, and combinations thereof.

In some embodiments, the decarboxylation and infusion apparatus described herein provides a means for a semi-automated system for performing the chemical processes of decarboxylating an organic material and infusing the decarboxylated organic material into a solvent for various applications, including consumption by a human. The apparatus may be provided as a single contained unit within a housing to prevent contamination, or undue transfer of the raw or processes materials.

The housing may be provided in various configurations to provide a single containerized heated reservoir and mixing chamber and mixing element to decarboxylate an organic material and infuse the organic material with a solvent. The infused solvent may then be extracted from the housing and packaged or otherwise processed into a final product.

The preferable heat-cooking steps may comprise only one dry heat cooking step, multiple dry heat-cooking steps, and/or dry heat-cooking step(s) with blended herbs, chemicals, and flavorings.

Many different embodiments have been disclosed herein, in connection with the above description. It will be understood that it would be unduly repetitious and obfuscating to literally describe every combination and subcombination of these embodiments. Accordingly, all embodiments can be combined in any way and/or combination, and the present specification, shall be construed to constitute a complete written description of all combinations and subcombinations of the embodiments described herein, and of the manner and process of making and using them, and shall support claims to any such combination or subcombination.

It will be appreciated by persons skilled in the art that the present embodiment is not limited to what has been particularly described hereinabove. A variety of modifications and variations are possible in light of the above teachings without departing from the following claims.

What is claimed is:

1. An apparatus for decarboxylating and infusing cannabis comprising:
   a) a housing containing a heated reservoir in operable communication with a user interface whereon a user selects decarboxylation and infusion settings, a mixing element to agitate cannabis, an airtight lid, a timer, memory, cannabis, an alert system, a solvent disposed therein and wherein said housing is encapsulated by an insulative layer; and
   b) a user interface provided on the decarboxylation and infusion apparatus to permit the user to select from a plurality of decarboxylation and infusion settings provided on a user interface on a housing of the decarboxylation and infusion apparatus, wherein another user interface is provided on a smart device which is in wireless communication with the decarboxylation and infusion apparatus.

* * * * *